(12) United States Patent
Smart

(10) Patent No.: US 10,413,382 B2
(45) Date of Patent: Sep. 17, 2019

(54) SANITARY MONITORING SYSTEM

(71) Applicant: Smartline Holdings Pty Ltd, Palmwoods, Queensland (AU)

(72) Inventor: William Hugh Dawkins Smart, Buderim (AU)

(73) Assignee: Smartline Holdings Pty Ltd, Palmwoods, Queensland (AU)

( * ) Notice: Subject to any disclaimer, the term of this patent is extended or adjusted under 35 U.S.C. 154(b) by 77 days.

(21) Appl. No.: 15/738,895

(22) PCT Filed: Jun. 27, 2016

(86) PCT No.: PCT/AU2016/050548
§ 371 (c)(1),
(2) Date: Dec. 21, 2017

(87) PCT Pub. No.: WO2016/205896
PCT Pub. Date: Dec. 29, 2016

(65) Prior Publication Data
US 2018/0177563 A1    Jun. 28, 2018

(30) Foreign Application Priority Data
Jun. 25, 2015    (AU) .............................. 2015902448

(51) Int. Cl.
*A61B 90/70*    (2016.01)
*A61B 1/00*    (2006.01)
*A61B 1/12*    (2006.01)
*B08B 3/10*    (2006.01)

(52) U.S. Cl.
CPC .......... *A61B 90/70* (2016.02); *A61B 1/00057* (2013.01); *A61B 1/00059* (2013.01); *A61B 1/123* (2013.01); *A61B 1/125* (2013.01); *B08B 3/10* (2013.01); *A61B 2090/701* (2016.02); *A61B 2090/702* (2016.02)

(58) Field of Classification Search
CPC .................................. A61B 90/70; A61B 1/00
See application file for complete search history.

(56) References Cited

U.S. PATENT DOCUMENTS

| | | | |
|---|---|---|---|
| 5,408,991 A | 4/1995 | Iida et al. | |
| 8,721,985 B2 | 5/2014 | Medici | |
| 9,561,129 B2* | 2/2017 | Ross | A61M 1/0035 |
| 9,592,517 B2* | 3/2017 | Kawakami | A61B 17/3203 |
| 9,889,239 B2* | 2/2018 | Michaels | A61M 1/0001 |
| 2005/0209507 A1 | 9/2005 | Suzuki et al. | |
| 2009/0192354 A1 | 7/2009 | Hasegawa | |
| 2009/0220377 A1 | 9/2009 | Hasegawa et al. | |

(Continued)

OTHER PUBLICATIONS

International Search Report and Written Opinion for International Application No. PCT/AU2016/050548 dated Oct. 28, 2016.

*Primary Examiner* — Jewel V Dowtin
(74) *Attorney, Agent, or Firm* — Wegman Hessler

(57) ABSTRACT

A sanitary monitoring system, the system including: one or more conduits configured to be connected to a medical device; one or more measurement devices configured to assist in determining one or more flow rates associated with the medical device from a fluid flow provided through the one or more conduits; and a status device configured to determine a sanitary condition of the medical device from the one or more flow rates.

22 Claims, 4 Drawing Sheets

(56) References Cited

U.S. PATENT DOCUMENTS

| | | |
|---|---|---|
| 2011/0097248 A1 | 4/2011 | Tomita et al. |
| 2013/0098400 A1 | 4/2013 | Nguyen et al. |
| 2018/0177563 A1* | 6/2018 | Smart ................ A61B 1/00057 |

* cited by examiner

SANITARY MONITORING SYSTEM

FIELD OF THE INVENTION

The invention relates to a sanitary monitoring system and method of use. In particular, the invention relates, but is not limited, to a sanitary monitoring system and method of use for a medical scope.

BACKGROUND TO THE INVENTION

Reference to background art herein is not to be construed as an admission that such art constitutes common general knowledge in Australia or elsewhere.

Medical devices are associated with a definitive risk of bacterial and fungal infections. To reduce the risk of infections, some medical devices are extensively cleaned after each use. For example, medical scopes such as endoscopes are normally washed and reused after each use as they are expensive to manufacture and hence to purchase.

Whilst cleaning medical scopes assist in reducing the risk of infection, determining whether the medical device has been adequately cleaned is difficult. A visual inspection gives a general indication that the medical device has been cleaned. However, internal components of the medical device may still be soiled.

Furthermore, ensuring that the internals of the medical device are dried within a predetermined time is a difficult task. As would be appreciated, failing to dry the medical device within a predetermined time may increase the risk of infection.

OBJECT OF THE INVENTION

It is an aim of this invention to provide a sanitary monitoring system and method of use which overcomes or ameliorates one or more of the disadvantages or problems described above, or which at least provides a useful alternative.

Other preferred objects of the present invention will become apparent from the following description.

SUMMARY OF INVENTION

In one form, although not necessarily the only or broadest form, the invention resides in a sanitary monitoring system, the system including:

one or more conduits configured to be connected to a medical device;

one or more measurement devices configured to assist in determining one or more flow rates associated with the medical device from a fluid flow provided through the one or more conduits; and a status device configured to determine a sanitary condition of the medical device from the one or more flow rates.

Preferably, the medical device is in the form of a scope. Typically, the medical device is in the form of a flexible scope or a rigid scope. Normally, the medical device is an endoscope, gastroscope, bronchoscope, duodenoscope, enterscope, ultrasound scope, toe probe, truss probe, Brachy probe and/or ENT flexible or rigid scope.

Normally, the medical device includes one or more ports to be respectively connected to the one or more conduits. Preferably, the one or more conduits include a releasable coupling to connect to the one or more ports. Typically, the one or more conduits include a valve that allows fluid flow when the one or more ports are connected thereto. Preferably, the one or more conduits are approximately 1.5 mm in diameter. Preferably, the diameter of the one or more conduits is used to restrict flow therethrough.

Preferably, the one or more conduits are connected to a hollow member. Preferably, the hollow member includes an inner hollow member and an outer hollow member. Normally, the hollow member is located in a medical container.

Preferably, the fluid flow is provided through the hollow member. Typically, the fluid flow is a vacuum such that fluid is drawn through the medical device, flows through the one or more conduits and then flows through the hollow member. Preferably, the fluid flow is provided by a pump. Alternatively, or additionally, the fluid flow is provided by a pressure difference or potential energy difference in the form of height.

Preferably, the hollow member is configured to support the medical device in a storage position. Normally, the hollow member includes at least one hanger thereon to support the medical device. Preferably, the at least one hanger is configured to rotate about the hollow member.

Typically, the one or more conduits are connected to an upper portion of the hollow member and/or a lower portion of the hollow member.

Preferably, the one or more measurement devices are connected to the one or more conduits. Typically, the one or more measurement devices are connected downstream of the one or more ports. Preferably, one of the one or more measurement devices are connected to the hollow member.

Preferably, the one or more measurement devices are in communication with the status device.

Normally, the one or more measurement devices are in the form of pressure sensors.

Preferably, the one or more measurement devices assist in determining the one or more flow rates associated with the medical device by communicating one or more pressures to the status device.

Typically, the one or more measurement devices assist in determining the one or more flow rates associated with the medical device by:

communicating one or more pressures from the one or more conduits to the status device; and communicating one or more pressures from the hollow member to the status device.

Preferably, the status device is configured to receive information associated with the medical device. Normally, the status device is configured to receive information associated with the medical device from a tag. Normally, the tag is a radio frequency identification (RFID) tag. Preferably, the RFID is active and includes its own power source. Alternatively, the RFID tag is passive and requires a power signal to operate.

Typically, the information associated with the medical device includes information relating to the one or more ports. Preferably, the information relating to the one or more ports includes a total number of ports. Normally, the information relating to the one or more ports includes a number of upper ports and a number of lower ports. Preferably, the upper ports are associated with a top handpiece of the medical device and the lower ports are associated with an umbilical cable.

Typically, the information associated with the medical device includes one or more aperture sizes. Preferably, the one or more aperture sizes relate to the one or more ports of the medical device. That is, preferably the information from the tag contains information relating to the size of each port in the medical device. Normally, the aperture size corresponds to an aperture size of the one or more conduits.

Preferably, the status device is configured to determine the one or more flow rates associated with the medical device based on the aperture size and a pressure difference. Normally, the pressure difference is between the one or more pressures from the one or more conduits and the one or more pressures from the hollow member.

Typically, the status device is configured to retrieve a minimum flow rate. Preferably, the minimum flow rate is associated with the medical device and/or the one or more conduits. Normally, the status device retrieves the minimum flow rate from the tag.

Preferably, the status device is configured to determine the sanitary condition of the medical device by comparing the minimum flow rate with the one or more flow rates. For example, in response to a flow rate within the one or more conduits being determined as lower than the minimum flow rate associated therewith, the status device determines that the medical device is soiled or alike (e.g. partially connected).

Typically, the status device is configured to determine the sanitary condition of the medical device by establishing whether the minimum flow rate associated with the medical device has been reached over a period of time. Reaching a minimum flow rate over a period of time accounts for a predetermined drying time.

Normally, the status device is configured to determine the sanitary condition of the medical device by establishing whether a port of the medical device is not connected to the one or more conduits. Typically, the status device determines when a port of the medical device is not connected to the one or more conduits by comparing the total number of ports to the one or more flow rates associated with the medical device.

For example, in response to receiving three flow rates associated with the medical device that has a total number of four ports, the status device is configured to determine that one port of the medical device is not connected.

Preferably, the status device is configured to determine the location of the port not connected to the one or more conduits. Typically, the status device determines the location of the port not connected to the one or more conduits by comparing the number of upper and lower ports with the one or more flow rates associated therewith. For example, if the medical device has three upper connections and two lower connections but there is only one flow rate from a lower connection, it can be substantially determine that a lower port is not connected to the one or more conduits.

Preferably, the status device is configured to determine the sanitary condition of the medical device by establishing whether a port of the medical device has been connected to a wrong conduit of the one or more conduits. Normally, the status device determines when the port of the medical device has been connected to wrong conduit of the one or more conduits based on the number of the ports, the location of the ports and/or the one or more flow rates.

Typically, the status device is configured to assist in alerting an operator that that sanitary condition of the medical device is unsatisfactory (i.e. in an unsanitary condition). Preferably, the status device is configured to assist in alerting an operator that the one or more conduits is not connected to the one or more ports and/or is connected to the wrong port. Normally, the status device is configured to indicate the location of the unconnected port(s) and/or wrongly connected port(s).

In another form the invention resides in a method for sanitary monitoring, the method including the steps of:
connecting a medical device to one or more conduits;
determining one or more flow rates associated with the medical device from a fluid flow provided through the one or more conduits; and
determining a sanitary condition of the medical device from the one or more flow rates.

Preferably, the step of connecting the medical device to the one or more conduits includes connecting one or more ports of the medical device to the one or more conduits.

Normally, the step of connecting the one or more ports of the medical device to the one or more conduits includes:
connecting one or more ports of the medical device to conduits located on an upper portion of a hollow member; and
connecting one or more ports of the medical device to conduits located on a lower portion of the hollow member.

Preferably, the step of determining the one or more flow rates associated with the medical device from a fluid flow provided through the one or more conduits includes measuring one or more pressures along the one or more conduits.

Typically, the step of determining the one or more flow rates associated with the medical device from a fluid flow provided through the one or more conduits includes measuring one or more pressures along the hollow member.

Preferably, the step of determining the one or more flow rates associated with the medical device includes defining a pressure difference. Normally, the pressure difference is between the one or more pressures along the one or more conduits and the one or more pressures along the hollow member.

Typically, the step of determining the one or more flow rates associated with the medical device includes retrieving one or more aperture sizes. Preferably, the one or more apertures sizes are related to the one or more ports.

Preferably, the step of determining the one or more flow rates associated with the medical device includes calculating the one or more flow rates based on the aperture size and the pressure difference.

Normally, the step of determining the sanitary condition from the one or more flow rates includes comparing the one or more flow rates with an associated minimum flow rate. Typically, the minimum flow rate is related to aperture size of the one or more ports. Preferably, the minimum flow rate allows a channel within the medical device to dry within a predetermined amount of time. Preferably, the minimum flow rate indicates that a channel within the medical device is clean.

Preferably, the step of determining the sanitary condition includes detecting whether one or more of the conduits are not connected to the one or more ports.

Normally, the step of detecting whether one or more of the conduits are not connected to the one or more ports includes:
determining the number of ports associated with the medical device;
comparing the number of ports with the number of flow rates; and
determining whether one or more of the ports are not connected based on the number of ports and the number of flow rates.

Preferably, in response to detecting an unconnected port, the method further includes determining the location of the unconnected port. Typically, the step of determining the location of the unconnected port includes:
retrieving one or more locations on where the pressure readings from the one or more conduits were taken;
retrieving the location of the one or more ports associated with the pressure readings; and comparing the location of the pressure readings with the location of the one or more ports to determine the location of the unconnected port.

Preferably, the step of determining whether the sanitary condition of the medical device from the one or more flow rates includes determining when the port of the medical device has been connected to wrong conduit of the one or more conduits based on the number of the ports, the location of the ports and/or the one or more flow rates.

Normally, the method further includes indicating that the medical device is unsanitary. Preferably, the method further includes indicating that a port is unconnected, partially connected and/or not connected to the correct conduit. Typically, the method further includes indicating the location of the unconnected port and/or wrongly connected port.

Further features and advantages of the present invention will become apparent from the following detailed description.

BRIEF DESCRIPTION OF THE DRAWINGS

By way of example only, preferred embodiments of the invention will be described more fully hereinafter with reference to the accompanying figures, wherein.

DETAILED DESCRIPTION OF THE DRAWINGS

Figure 1:
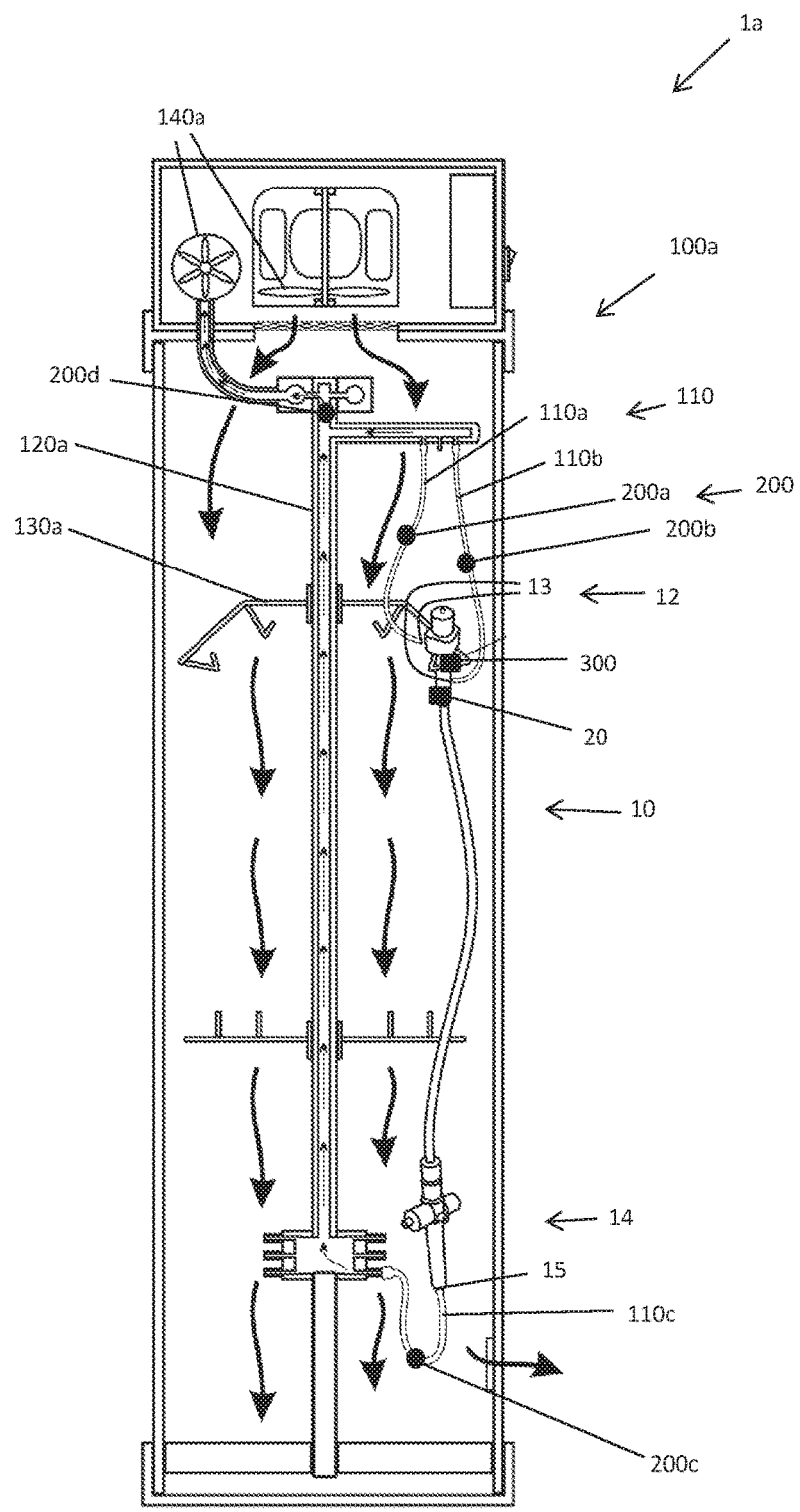
FIG. 1 illustrates a sanitary monitoring system according to an embodiment of the invention.

FIG. 1 illustrates a sanitary monitoring system 1a according to an embodiment of the invention. The sanitary monitoring system 1a includes a medical device in the form of a scope 10, a tag 20, conduits 110 located in a medical container 100a, measurement devices 200 and a status device 300.

At the outset, it is noted that in this disclosure the use of a reference numeral followed by a lower case letter indicates alternative embodiments of a general element identified by the reference numeral. Thus for example an upper conduit 110a is similar to but not identical to a lower conduit 110c. Further, references to an element identified only by the numeral refer to all embodiments of that element. Thus for example a reference to conduits 110 is intended to include both the upper conduit 110a and the lower conduit 110c.

The scope 10 includes an upper portion in the form of handpiece 12 and a lower portion in the form of umbilical cable 14. The handpiece 12 includes two upper ports 13 and the umbilical cable 14 includes a lower port 15. As would be appreciated, the upper and lower ports 13, 15 are connected to channels that extend along the internals of the scope 10.

The tag 20 is attached to the scope 10. The tag 20 is in the form of an active radio frequency identification (RFID) tag in this embodiment. However, it would be appreciated that the tag 20 may be passive and require a power signal from a reader device to operate. The tag 20 is configured to store and process information along with transferring and receiving information. In this embodiment, the tag 20 stores and transfers information relating to the aperture size of the ports 13, 15, the number of ports 13, 15, the location of the ports 13, 15 and minimum flow rates associated with the scope 10. The minimum flow rates associated with the scope 10 relate to minimum air flow rates required through the channels within the scope 10 to ensure that the channels are not soiled (i.e. blocked) and can dry within a predetermined time.

The conduits 110 in this embodiment include upper conduits 110a, 110b and lower conduit 110c. The upper conduits 110a, 110b are configured to be connected to the upper ports 13. The lower conduit 110c is configured to be connected to the lower port 15. The conduits 110 are connected to a hollow member 120a inside the medical container 100a. The hollow member 120a also provides storage support for the scope 10. In particular, connected to the hollow member 120a is a rotatable hanger 130a that provides storage support to the scope 10.

The medical container 100a also includes pumps 140a. The pumps 140a work in conjunction such that a vacuum is created in the medical container 100a whereby air is i) drawn into the channels of the scope 10; ii) flows through the ports 13, 15; iii) flows through the conduits 110; and iv) then flows through the hollow member 120a.

The measurement devices 200 in this embodiment are in the form of pressure sensors. Measurement devices 200a, 200b are connected to upper conduits 110a, 110b, respectively. Measurement device 200c is connected to lower conduit 110c. Further measurement device 110d is connected downstream of the measurement devices 110a, 110b, 110c to the hollow member 120a.

The status device 300 is located on the hanger 130a in the medical container 100a such that when the scope 10 is connected to the hanger 130a, the status device 300 is in communication with the tag 20. Further to the above, the status device 300 is configured to retrieve information from the tag 20 relating to the aperture size of the ports 13, 15, the number of ports 13, 15, the location of the ports 13, 15 and the minimum flow rates associated with the scope 10 (i.e. minimum flow rates through the channels, ports 13, 15 and/or conduits 110).

The status device 300 is also in communication with the measurement devices 200. That is, pressures measured by the measurement devices 200 are communicated to the status device 300. Furthermore, the status device 300 is configured to allocate the measurement devices 200 to a location. For example, the status device 300 may allocate the measurement devices 200a, 200b at an upper location and the measurement device 200c as a lower location.

The status device 300 is configured to determine flow rates associated with the scope 10 in this embodiment. That is, from pressures received from the measurement devices 200, the status device 300 is configured to calculate flow rates associated with the conduits 110 using the aperture sizes of each related port 13, 15.

In particular, the status device 300 is configured to define respective pressure differences between each measurement device 200a, 200b, 200c, connected to the conduits 110, and the measurement device 200d, connected to the hollow member 120. From these respective pressure differences, the status device 300 is configured to calculate the flow rates in each conduit 110 using the respective aperture sizes of the ports 13, 15 retrieved from the tag 20. As would be appreciated, the flow rates in each conduit 110 have an association with the flow rates through each related port 13, 15 and channels connected thereto.

From the flow rates associated with the scope 10 (i.e. the flow rates through the conduits 110), the status device 300 is configured to determine whether the channels within the scope 10 are soiled, whether a conduit 110 is not connected or is partially connected to one of the ports 13, 15 and/or whether one of the conduits 110 have been connected to an incorrect port 13, 15. As would be appreciated, all of the above situations are indications that the scope 10 is in a sanitary condition that is unsatisfactory (i.e. an unsanitary condition).

In order to determine whether a conduit 110 is not connected to the ports 13, 15, the status device 300 is configured to compare the information relating to the number of ports 13, 15 and the measurements of the measurement devices 200. This is outlined further below. In addition, the status device 300 is configured to determine a location of the unconnected port 13, 15 from the measurements of the measurement devices 200. This again is outlined further below.

With regards to determining whether the scope 10 is soiled or unsoiled (i.e. the sanitary condition), the status device 300 is configured to compare the flow rates associated with scope 10 and the minimum flow rates associated therewith from the tag 20. If the flow rates associated with the scope 10 are below the minimum flow rates associated therewith, this is an indication that the internal channels or ports 13, 15 of the scope 10 are soiled. Alternatively, it may indicate that a further problem in the system 1 (e.g. there is a loose connection between the conduit 110a and port 13 and/or conduit 110a is connected to the wrong port 15).

In the event that the status device 300 determines that the scope 10 is soiled, not connected to conduits 110 or incorrectly connected to the conduits 110, the status device 300 is configured to provide an indication to a user of the associated problem (i.e. scope 10 is soiled, not connected, partially connected and/or incorrectly connected). Furthermore, the status device 300 may also give an indication of the location where the scope 10 is not connected to the conduits 110 (i.e. an upper conduit 110a, 110b or a lower conduit 110c).

In addition, the status device 300 may be configured to record the associated problem (i.e. scope 10 is soiled, not connected, partially connected and/or incorrectly connected) on the tag 20 such that auditing or future processes can be decided having this information. Alternatively, or additionally, data from the status device 300 relating to the scope 10 may be directed to a monitoring network. It would be appreciated that the status device 300 may only report associated problems to the network to minimising data packet traffic on the network.

Figures 2, 3:
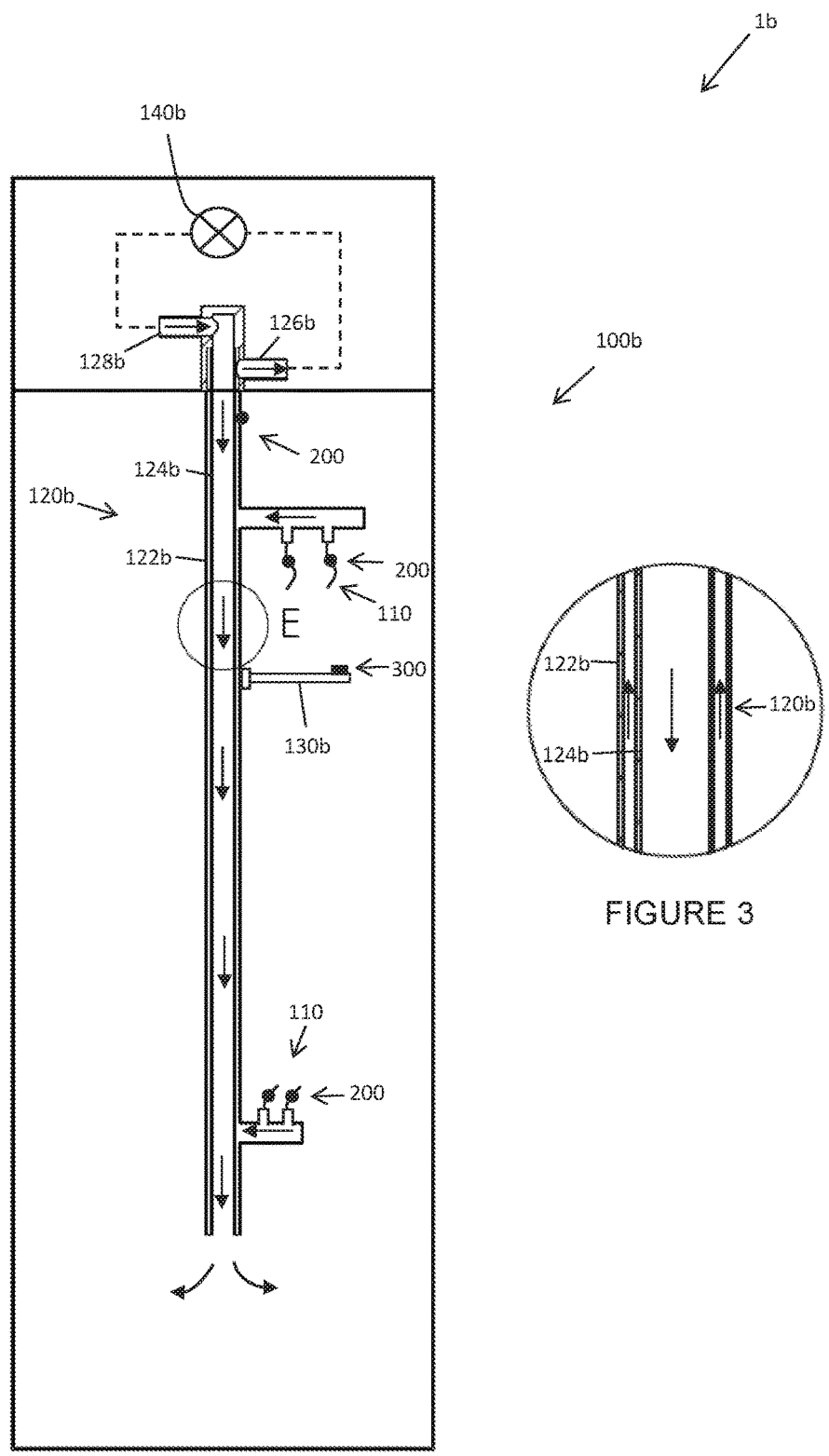
FIG. 2 illustrates a section schematic view of a sanitary monitoring system according to a further embodiment of invention.
FIG. 3 illustrates a close up view of part of the sanitary monitoring system shown in FIG. 2.

FIG. 2 illustrates a section schematic view of a sanitary monitoring system 1b according to a further embodiment of invention. The scope 10 is not shown in the sanitary monitoring system 1b but the sanitary monitoring system 1b is substantially similar to the sanitary monitoring system 1a. Like numbering has therefore been used between FIGS. 1 and 2. However, a notable difference between the sanitary monitoring systems 1a, 1b is the hollow member 120b.

The hollow member 120b includes an outer hollow member 122b and an inner hollow member 124b. The outer hollow member 122b is sealed at either end with the assistance of the inner hollow member 124b. The inner hollow member 124b is open to the cabinet 100b at one end.

Airflow is provided into the cabinet 100b through the inner hollow member 124b. The inner hollow member 124b is connected an outlet of a pump 140b via connector 128b. The airflow through the inner hollow member 124b is delivered to a lower portion of the cabinet 100b.

Air is withdrawn from the cabinet 100b via the outer hollow member 122b. The outer hollow member 122b is connected to an inlet of the pump 140b via connector 126b. The outer hollow member 122b is also in fluid communication with the conduits 110 to draw air through the scope 10 from the cabinet 100b.

Airflow through the inner and outer hollow members 122b, 124b is shown further in FIG. 3. FIG. 3 illustrates a close up view of section E shown in FIG. 2.

Figure 4:
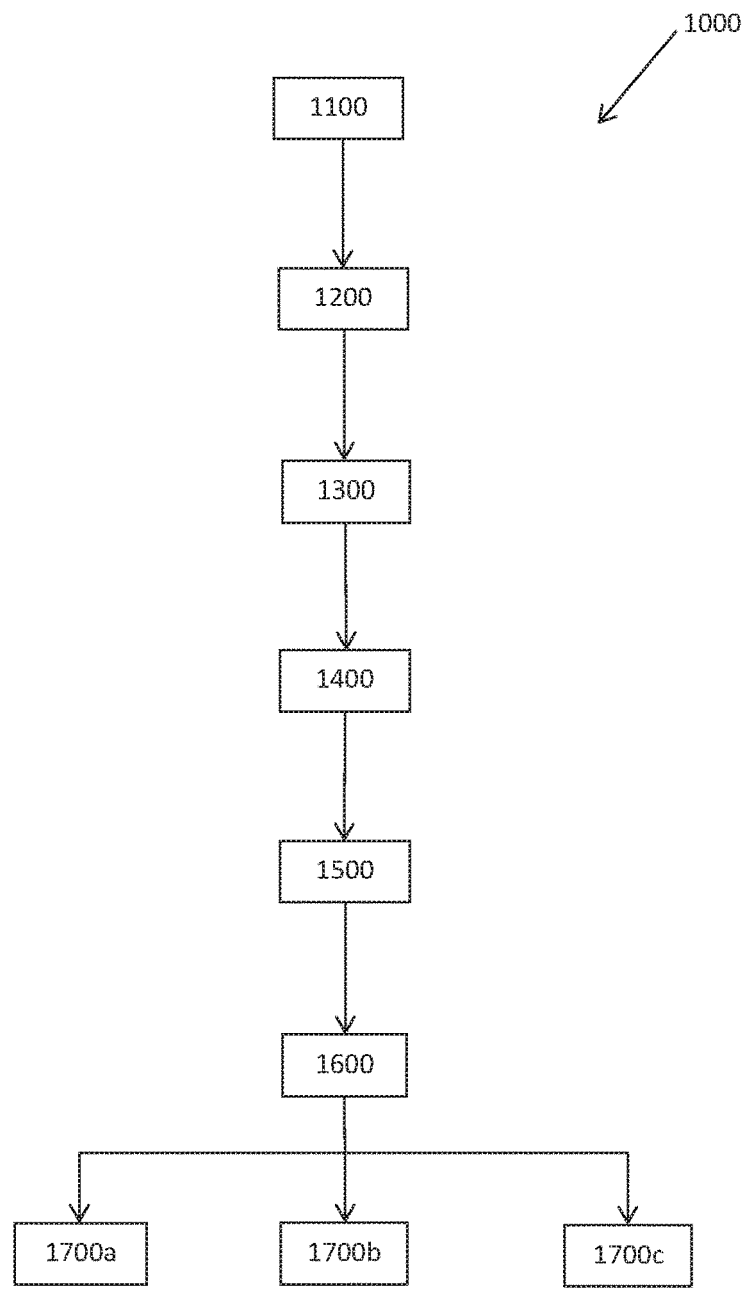
FIG. 4 illustrates a method for sanitary monitoring according to an embodiment of the invention with reference to FIGS. 1 and 2.
Figure 5:
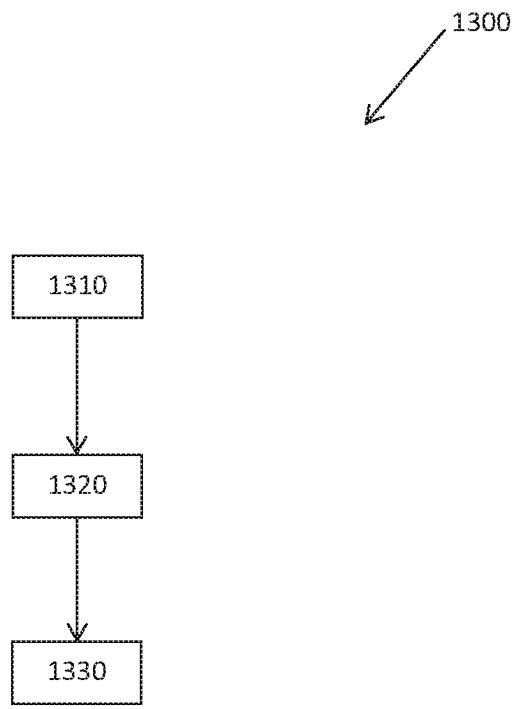
FIG. 5 illustrates part of the method illustrated in FIG. 4, according to an embodiment of the invention.

FIG. 4 outlines a method for sanitary monitoring 1000 with reference to FIG. 1 and FIG. 2.

At step 1100, an operator washes the scope 10. Normally, manual washing of the scope 10 takes place in a number of stages and, thereafter, an automatic washing unit is used to complete cleaning of the scope 10.

At step 1200, the operator visually inspects the scope 10 to determine whether any contaminants remain on the outside of the washed scope 10.

At step 1300, after passing visual inspection, the operator loads the scope 10 into the medical container 100. Loading the scope 10 into the medical container 100 is outlined further in FIG. 3.

At step 1310, the operator opens a door of the medical container 100. The operator may be required to swipe an identification tag to open the door of the medical container 100.

Following this, at step 1320, the operator places the scope 10 on the hanger 130. This supports the scope 10 above a floor of the medical container 100 such that the scope 10 hangs substantially in a vertical direction.

At step 1330, the operator connects the conduits 110 to the ports 13, 15 of the scope 10. That is, the operator connects the upper conduits 110a, 110b to the upper ports 13 and the lower conduit 110c to the lower port 15.

At step 1400, the status device 300 retrieves information from the tag 20. The status device 300 is triggered to obtain information from the tag 20 when they come into proximity with each other. Communication may be slightly delayed to allow adequate time for the operator to connect the conduits 110 to the ports 13, 15. The status device 300 obtains information from the tag 20 in the form of the aperture sizes of the ports 13, 15, the number of ports 13, 15, the location of the ports 13, 15 and the minimum flow rates associated with the scope 10 (i.e. minimum flow through the channels, ports 13, 15 and/or conduits 110).

At step 1500, the status device 300 calculates associated flow rates through the scope 10. The associated flow rates through the scope 10 in this embodiment are calculated through each of the conduits 110. As would be appreciated, the flow through the conduits 110 is substantially the same as through the respective channels and ports 13, 15 of the scope 10.

With the above in mind, to calculate the flow rate through each conduit 110a, 110b, 110c the status device 300 defines a pressure difference between each of the measurement devices 200a, 200b, 200c and the measurement device 200d connected to the hollow member 120. As would be appreciated by a person skilled in the art, the pressure difference between each measurement devices 200a, 200b, 200c and the measurement device 200d is indicative of the dynamic pressure in each conduit 110a, 110b, 110c.

In this regard, as the aperture size (i.e. diameter) of the conduits 110 is substantially the same as the aperture size (i.e. diameter) of each port 13, 15, retrieved from the tag 20, the status device 300 is then configured to calculate the flow rate through each conduit 110*a*, 110*b*, 110*c* based on the pressure differences above and the aperture size of each port 13, 15.

At step 1600, the status device 300 compares the flow rate through each conduit 110*a*, 110*b*, 110*c* with the minimum flow rates retrieved from the tag 20. The minimum flow rates are specific to each conduit 110*a*, 110*b*, 110*c*.

At step 1700*a*, in response to the status device 300 determining that the flow rate through each conduit 110*a*, 110*b*, 110*c* is higher than the minimum flow rate associated therewith, the status device 300 is configured to indicate that the flow through each conduit 110*a*, 110*b*, 110*c* (or each channel in the scope 10) is adequate. Having an adequate flow through each conduit 110*a*, 110*b*, 110*c* is indicative of the internals of the scope 10 being adequately sanitised. Furthermore, having an adequate flow through each conduit 110*a*, 110*b*, 110*c* substantially ensures that the internals of the scope 10 are dried within a predetermined time.

At step 1700*b*, in response to the status device 300 determining that the flow rate through one or more of the conduits 110*a*, 110*b*, 110*c* is lower than the minimum flow rate associated therewith, the status device 300 is configured to indicate that the flow through the specific conduit(s) 110*a*, 110*b*, 110*c* (or their related channel in the scope 10) is inadequate. Having an inadequate flow through one or more conduits 110*a*, 110*b*, 110*c* is indicative of the internals of the scope 10 being inadequately sanitised, one or more of the ports 13, 15 of the scope 10 not being adequately connected to the conduits 110 and/or one or more of the ports 12, 15 being connected to the wrong conduit 110.

At step 1700*c*, in response to the status device 300 receiving one or more measurements from the flow devices 200 that is less than the total number of ports 13, 15, the status device 300 is configured to indicate that one or more of the conduits 110 are not connected to the ports 13, 15. Furthermore, by comparing the location of the ports 13, 15 with the location of flow devices 200 not receiving a change in measurement, the status device 300 may also determine and indicate the location of the unconnected port 13, 15, Moreover, in view of the above, it would be appreciated that there may be alternation between the steps 1700*a*, 1700*b* and 1700*c*. For example, upon detecting that the one or more of the conduits 110 are not connected to the ports 13, 15 at step 1700*c*, the operator may connect the conduit 110 to one of the ports 13, 15. Upon connecting the port 13, 15, the status device 300 may then indicate that the scope 10 is unsanitary at step 1700*b*, after proceeding through steps 1500, 1600 again, and provide an indication that the scope 10 needs to be re-cleaned.

Furthermore, it would be appreciated that the status device 300 may indicate steps 1700*a*, 1700*b* and/or 1700*c* through a network to a user. It may also record information relating to steps 1700*a*, 1700*b* and/or 1700*c* on the tag 20 for auditing and/or determining whether the scope 10 is fit for use in a further process.

The sanitary monitoring system 1 and method 1000 monitor that each conduit 110 is correctly connected, is connected in the correct location and has correct airflow. This is achieved by, for example, the programming of the tag 20 to include characteristics of each scope 10 and the flow devices 200 providing indications of flow (i.e. pressure) to the status device 300.

The sanitary monitoring system 1 and method 1000 therefore substantially ensure that i) the flow rate of air through each channel in the scope 10 is such that a drying cycle within a designated time is achieved; and ii) the channels within the scope 10 are substantially clean. A flow rate failure or failure to connect, for example, creates an alert to the operator that the scope 10 may not be fit for use. This assists in reducing the risk of infection.

Moreover, the sanitary monitoring system 1 and method 1000 allow processes related to the scope 10 to be recorded for later auditing and/or risk management assessments.

The sanitary monitoring system 1 and method 1000 also reduces the amount of processing and reprocessing required for the scope 10. Furthermore, the sanitary monitoring system 1 and method 1000 can work with either pressure or a vacuum.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step etc.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

In this specification, the terms 'comprises', 'comprising', 'includes', 'including', or similar terms are intended to mean a non-exclusive inclusion, such that a method, system or apparatus that comprises a list of elements does not include those elements solely, but may well include other elements not listed.

The claims defining the invention are as follows:

1. A sanitary monitoring system for a medical device having a plurality of ports and an internal channel, the system comprising:
    a container having a fluid pump to pump fluid into the container and at least one discharge port for the discharge of fluid from the container;
    one or more conduits configured to be connected to the medical device and to be in fluid communication with the at least one discharge port;
    one or more measurement devices configured to assist in determining one or more flow rates of fluid drawn through the one or more conduits; and
    a status device configured to determine a sanitary condition of the medical device from the one or more flow rates.

2. The system of claim 1, wherein the container further comprises an extraction pump configured to be at or near the at least one discharge port, wherein said one or more conduits are in fluid communication with the extraction pump, and
    wherein in use the fluid passes through the medical device, the one or more conduits, and is discharged through the extraction pump and the at least one discharge port.

3. The system of claim 1, wherein the one or more conduits are configured to be connected to a hollow member, said hollow member is configured to be in fluid communication with the at least one discharge port.

4. The system of claim 3, wherein the one or more measurement devices assist in determining the one or more flow rates associated with the medical device by communicating one or more pressures from the one or more conduits to the status device; and communicating one or more pressures from the hollow member to the status device.

5. The system of claim 1, wherein the status device is configured to receive information associated with the medical device, said information comprises data relating one or more aperture sizes of one or more ports of the medical device.

6. The system of claim 5, wherein the status device is configured to determine the one or more flow rates associated with the medical device based on the one or more aperture sizes and a pressure difference.

7. The system of claim 6, wherein the status device is configured to retrieve a minimum flow rate and determine the sanitary condition of the medical device by comparing the minimum flow rate with the one or more flow rates.

8. The system of claim 7, wherein the status device is configured to determine the sanitary condition of the medical device by establishing whether the minimum flow rate associated with the medical device has been reached over a period of time.

9. The system of claim 1, wherein the status device is configured to determine the sanitary condition of the medical device by establishing whether a port of the medical device is not connected to the one or more conduits.

10. The system of claim 9, wherein the status device is configured to determine the location of the medical device port that is not connected to the one or more conduits.

11. The system of claim 1, wherein the status device is configured to determine the sanitary condition of the medical device by establishing whether a port of the medical device has been connected to a wrong conduit of the one or more conduits.

12. The system of claim 1, wherein the status device is configured to alert an operator that the sanitary condition of the medical device is unsatisfactory.

13. A method for sanitary monitoring of a medical device having a plurality of ports and at least one internal channel using a sanitary system comprising:
 a container having a fluid pump to pump fluid into the container and at least one discharge port for the discharge of fluid from the container;
 one or more conduits configured to be connected to the medical device and to be in fluid communication with the at least one discharge port;
 one or more measurement devices configured to assist in determining one or more flow rates of fluid drawn through the one or more conduits; and
 a status device configured to determine a sanitary condition of the medical device from the one or more flow rates;
  wherein the method comprises the steps of:
   connecting the medical device to the one or more conduits;
   determining the one or more flow rates associated with the medical device from a fluid flow drawn through the one or more conduits; and
   determining the sanitary condition of the medical device from the one or more flow rates.

14. The method of claim 13, wherein the container further comprises an extraction pump configured to be at or near the at least one discharge port, wherein said one or more conduits are in fluid communication with the extraction pump, and
 wherein in use the fluid passes through the medical device, the one or more conduits, and is discharged through the extraction pump and the at least one discharge port.

15. The method of claim 13, wherein the step of connecting the medical device to the one or more conduits includes connecting the plurality of ports of the medical device to the one or more conduits.

16. The method of claim 13, wherein the step of determining the sanitary condition of the medical device from the one or more flow rates includes detecting whether one or more of the conduits are not connected to the plurality of ports.

17. The method of claim 16, wherein the step of detecting whether one or more of the conduits are not connected to the plurality of ports of the medical device includes:
 determining the number of ports associated with the medical device;
 comparing the number of ports with the number of flow rates; and
 determining whether one or more of the plurality of ports are not connected based on the number of ports and the number of flow rates.

18. The method of claim 17, wherein in response to detecting an unconnected port, the method further includes determining the location of the unconnected port.

19. The method of claim 18, wherein the step of determining the one or more flow rates associated with the medical device from the fluid flow drawn through the one or more conduits includes measuring one or more pressures along the one or more conduits.

20. The method of claim 13, wherein the step of determining the one or more flow rates associated with the medical device from the fluid flow drawn through the one or more conduits includes defining a pressure difference between the one or more pressures along the one or more conduits and the one or more pressures along a hollow member.

21. The method of claim 13, wherein the step of determining the sanitary condition of the medical device from the one or more flow rates includes comparing the one or more flow rates with an associated minimum flow rate.

22. The method of claim 13, wherein the step of determining the sanitary condition of the medical device from the one or more flow rates includes determining when a port of the medical device has been connected to a wrong conduit of the one or more conduits.

* * * * *